US011042044B2

United States Patent
Abbasi et al.

(10) Patent No.: US 11,042,044 B2
(45) Date of Patent: Jun. 22, 2021

(54) CONTACT LENS CONTAINING A PHOTONIC CRYSTAL

(71) Applicant: Imam Abdulrahman Bin Faisal University, Dammam (SA)

(72) Inventors: Badaruddin Abbasi, Dammam (SA); Naif Nasser Almasoud, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 376 days.

(21) Appl. No.: 15/789,440

(22) Filed: Oct. 20, 2017

(65) Prior Publication Data

US 2018/0267331 A1 Sep. 20, 2018

Related U.S. Application Data

(60) Provisional application No. 62/472,857, filed on Mar. 17, 2017.

(51) Int. Cl.
  *G02C 7/04* (2006.01)
  *B29D 11/00* (2006.01)
  *A61B 5/1455* (2006.01)
  *A61B 5/145* (2006.01)
  *A61B 5/00* (2006.01)

(52) U.S. Cl.
  CPC ........ *G02C 7/049* (2013.01); *B29D 11/00807* (2013.01); *G02C 7/04* (2013.01); *A61B 5/14532* (2013.01); *A61B 5/14551* (2013.01); *A61B 5/6821* (2013.01); *B29D 11/00038* (2013.01)

(58) Field of Classification Search
  CPC ............ A61B 5/6821; B29D 11/00038; B29D 11/00807; G02C 7/04; G02C 7/049
  See application file for complete search history.

(56) References Cited

U.S. PATENT DOCUMENTS

| | | |
|---|---|---|
| 8,877,227 B2 | 11/2014 | Ravi |
| 2008/0157035 A1 | 7/2008 | Alexeev |
| 2010/0113901 A1 | 5/2010 | Zhang et al. |
| 2015/0173658 A1* | 6/2015 | Liu ...................... A61B 5/0031 600/348 |
| 2015/0201837 A1* | 7/2015 | Song .................... A61B 5/0002 600/345 |

FOREIGN PATENT DOCUMENTS

CN    103605215    1/2015

OTHER PUBLICATIONS

Jia-Li Ruan et al., "A Gelated Colloidal Crystal Attached Lens for Noninvasive continuous Monitoring of Tear Glucose," Polymers, Mar. 28, 2017, 12 Pages.
Vladimir L. Alexeev et al., "Photonic Crystal Glucose-Sensing Material for Noninvasive Monitoring of Glucose in Tear Fluid," Clinical Chemistry, Sep. 1, 2004, vol. 50, No. 12, pp. 2353-2360.

* cited by examiner

*Primary Examiner* — Puya Agahi
(74) *Attorney, Agent, or Firm* — Oblon, McClelland, Maier & Neustadt, L.L.P.

(57) ABSTRACT

A contact lens containing a photonic crystal which is configured to change color depending on a concentration of an analyte in the tears of a subject. The change in color is reversible. The contact lens may be useful for monitoring the concentration of glucose in tears of a diabetic subject or a prediabetic subject.

20 Claims, 13 Drawing Sheets

FIG. 8A
FIG. 8B
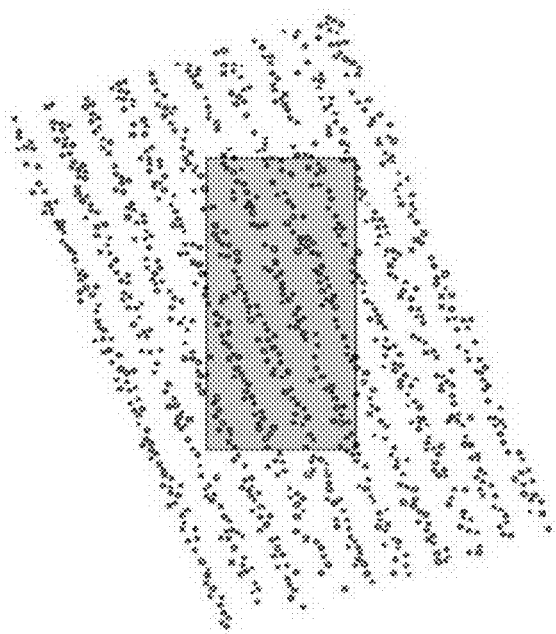
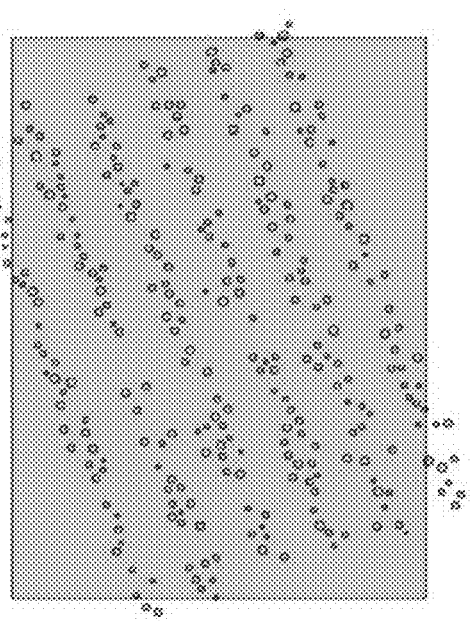
FIG. 8C
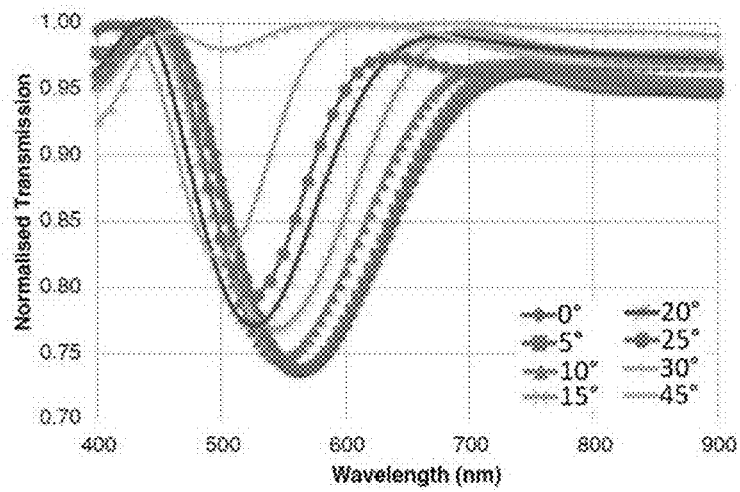

CONTACT LENS CONTAINING A PHOTONIC CRYSTAL

CROSS-REFERENCE TO RELATED APPLICATIONS

This application claims the priority of the filing date of the U.S. provisional patent application No. 62/472,857 filed Mar. 17, 2017, the disclosure of which is hereby incorporated herein by reference in its entirety.

STATEMENT REGARDING PRIOR DISCLOSURES BY THE INVENTORS

Aspects of this technology are described in an article "Parametric Simulations of Slanted 1D Photonic Crystal Sensors" by Aaron Breuer-Weil, Naif Nasser Almasoud, Badaruddin Abbasi, Ali K. Yetisen, Seok-Hyun Yun. and Haider Butt, in Nanoscale Research Letters, 2016, 11:157, which is incorporated herein by reference in its entirety.

BACKGROUND

Field of the Disclosure

This disclosure relates to a contact lens containing a photonic crystal which senses the level of analyte(s) in the tears of the wearer.

Description of the Related Art

Photonic crystals have been used in a range of applications such as optical waveguides, solar-cells, improved optic fibers, live virus detectors, and medical diagnostics (Johnson S G et al. (2000) Linear waveguides in photonic-crystal slabs. Phys Rev B 62(12):8212-8222; Moreno E, Garcia-Vidal F J, Martín-Moreno L (2004) Enhanced transmission and beaming of light via photonic crystal surface modes. Phys Rev B 69(12):121402; Butt H et al. (2011) Plasmonic band gaps and waveguide effects in carbon nanotube arrays based metamaterials. ACS Nano 5(11):9138-9143; Bermel P et al. (2007) Improving thin-film crystalline silicon solar cell efficiencies with photonic crystals. Opt Express 15(25): 16986-17000; Knight J C (2003) Photonic crystal fibres. Nature 424(6950):847-851; Yanik A A et al. (2010) An optofluidic nanoplasmonic biosensor for direct detection of live viruses from biological media. Nano Lett 10(12):4962-4969; and Farandos N M et al. (2015) Contact lens sensors in ocular diagnostics. Adv Healthc Mater 4(6):792-810, each incorporated herein by reference in their entirety). The research in photonic crystals has advanced significantly over the last decade (Fang Y et al. (2015) Reconfigurable photonic crystals enabled by pressure-responsive shape-memory polymers. Nat Commun 6:7416; Naydenova I et al. (2015) Hybrid sensors fabricated by inkjet printing and holographic patterning. Chem Mater 27(17):6097-6101; and Yetisen A K et al. (2016) Photonic hydrogel sensors. Biotechnology Advances. doi:10.1016/j.biotechadv.2015.10.005, each incorporated herein by reference in their entirety). Photonic crystals can be fabricated from nanoparticle-based structures containing alternating stacks of materials possessing different dielectric constants. The structures can be one-dimensional, two-dimensional, or three-dimensional.

In 1D photonic crystals the alternating dielectric constant only exists in one direction (Fang Y et al. (2013) Scalable bottom-up fabrication of colloidal photonic crystals and periodic plasmonic nanostructures. J Mater Chem C 1(38): 6031-6047: and Butt H et al. (2012) Negative index photonic crystal lenses based on carbon nanotube arrays. Photonics Nanostruct Fundam Appl 10(4):499-505, each incorporated herein by reference in their entirety). The 1D photonic crystals are commonly in a Bragg mirror configuration, and these structures act as efficient reflectors of specific wavelengths of electromagnetic radiation (photonic stopband) (Butt H et al. (2011) Enhanced reflection from arrays of silicon based inverted nanocones. Appl Phys Lett 99(13): 133105, incorporated herein by reference in its entirety). They restrict further propagation of the electromagnetic radiation with these wavelengths through the lattice. Instead, the electromagnetic radiation is reflected (Butt H et al. (2011) Photonic crystals & metamaterial filters based on 2D arrays of silicon nanopillars. Prog Electromagn Res 113: 179-194, incorporated herein by reference in its entirety). The band gap is brought about by constructive interference of reflected waves travelling through the lattice. The photonic band gap effect is highly desirable and can be used in both reflective and antireflective coatings, laser cavity end mirrors, and functionalized medical devices (Murtaza S S et al. (1995) High-reflectivity Bragg mirrors for optoelectronic applications. Quantum Electronics, IEEE Journal of 31(10): 1819-1825; and Ko D-H et al. (2013) A nano-patterned photonic crystal laser with a dye-doped liquid crystal. Appl Phys Lett 103(5):051101, each incorporated herein by reference in their entirety).

A relatively cost-effective method for making a tunable photonic crystal is a laser-based photochemical patterning (Yetisen A K et al. (2014) Light-directed writing of chemically tunable narrow-band holographic sensors. Adv Opt Mater 2(3):250-254; and Yetisen A K et al. (2014) Mechanism of multiple grating formation in high-energy recording of holographic sensors. Appl Phys Lett 105(26):261106, each incorporated herein by reference in their entirety). The tunable photonic crystal changes its periodicity to vary the specific wavelengths of light to be reflected, thus the crystal is tunable and the change in periodicity is reversible. When compared to other optical filtering techniques, such as plasmonic nanoparticle films, the photonic crystal offers dynamic and reversible tunability within the hydrogel volume (Zhang X-Y et al. (2011) Self-assembly of large-scale and ultrathin silver nanoplate films with tunable plasmon resonance properties. ACS Nano 5(11):9082-9092; and Isozaki K et al. (2010) Chemical coating of large-area Au nanoparticle two-dimensional arrays as plasmon-resonant optics. Appl Phys Lett 97(22):221101, each incorporated herein by reference in their entirety). Sensors based on 1D photonic crystals have been simulated (Tsangarides C P et al. (2014) Computational modelling and characterization of nanoparticle-based tunable photonic crystal sensors. RSC Adv 4(21):10454-10461, incorporated herein by reference in its entirety).

In view of the foregoing, it is an objective of the present disclosure to provide a contact lens containing a photonic crystal and a method of using the contact lens to monitor glucose level in tears of the wearer (i.e., subject).

SUMMARY

A first aspect of the disclosure relates to a contact lens, comprising a photonic crystal comprising: (i) a plurality of metal nanoparticle stacks comprising metal nanoparticles, wherein the plurality of metal nanoparticle stacks are spaced such that each metal nanoparticle stack is substantially parallel to one another, and (ii) a hydrogel matrix comprising polyhydroxyethylmethacrylate; wherein the plurality of metal nanoparticle stacks is arranged within the hydrogel matrix.

In one embodiment, the metal nanoparticles comprise at least one metal selected from the group consisting of silver, gold, titanium, platinum, iron, cobalt, chromium, molybdenum, vanadium, tin, nickel, and niobium.

In one embodiment, each metal nanoparticle stack comprises 20-200 metal nanoparticles.

In one embodiment, the photonic crystal comprises up to 100 metal nanoparticle stacks.

In one embodiment, the photonic crystal comprises 3-6 metal nanoparticle stacks.

In one embodiment, a distance between adjacent metal nanoparticle stacks is in a range of 140-250 nm.

In one embodiment, the plurality of metal nanoparticle stacks has a tilt angle in a range of 1-30° measured from a plane of a metal nanoparticle stack to a surface plane of the photonic crystal.

In one embodiment, the metal nanoparticles are substantially spherical.

In one embodiment, the metal nanoparticles have an average diameter in a range of 2-20 nm.

In one embodiment, the average diameter of the metal nanoparticles varies between each metal nanoparticle stack.

In one embodiment, the metal nanoparticles are randomly dispersed within each metal nanoparticle stack.

In one embodiment, each metal nanoparticle stack comprises metal nanoparticles of substantially uniform diameter.

In one embodiment, a distance between the adjacent metal nanoparticle stacks increases or decreases in response to a concentration of an analyte thereby producing a shift in a photonic band gap and a color change in the photonic crystal.

In one embodiment, the shift in the photonic band gap is reversible.

In one embodiment, the color change is reversible.

In one embodiment, the analyte is glucose.

In one embodiment, the contact lens further comprises a sensor for measuring the shift in photonic band gap.

A second aspect of the disclosure relates to a method for detecting a glucose concentration of a subject, the method comprising: wearing the contact lens of the first aspect, thereby contacting the contact lens to tears produced by the subject; and detecting the shift in the photonic band gap.

In one embodiment, the photonic crystal changes color in response to the glucose concentration in the tears.

In one embodiment, the subject has diabetes.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 8A shows the tilted lattice arrangement of metal nanoparticles.

FIG. 8B shows large gaps are present in the geometry of the photonic crystal when a regular lattice is used.

FIG. 8C is an overlay of the transmission spectra for photonic crystals with different lattice tilt angles.

DETAILED DESCRIPTION OF THE PREFERRED EMBODIMENTS

An aspect of the disclosure relates to a contact lens 100 including a photonic crystal 108 containing a hydrogel matrix comprising polyhydroxyethylmethacrylate and a plurality of metal nanoparticle stacks comprising metal nanoparticles.

The contact lens 100 may be a soft contact lens, a hard contact lens, or a hybrid contact lens. The contact lens may be a non-hydrous contact lens or a hydrous contact lens. The contact lens 100 is preferably a soft contact lens, and more preferably a silicone hydrogel contact lens. The contact lens 100 may be produced by methods known to those of ordinary skill in art. The method of making the contact lens 100 disclosed herein may be similar to the method of making hybrid contact lens and/or colored contact lens (U.S. Pat. No. 4,701,288 A assigned to Bausch and Lomb; U.S. Pat. No. 7,163,292 B2 assigned to Synergeyes; and U.S. Pat. No. 9,346,194 B2 assigned to Novartis AG, each incorporated herein by reference in its entirety). In some embodiments, the contact lens 100 may be produced by a lathe cutting process or an injection molding process.

Figure 11:
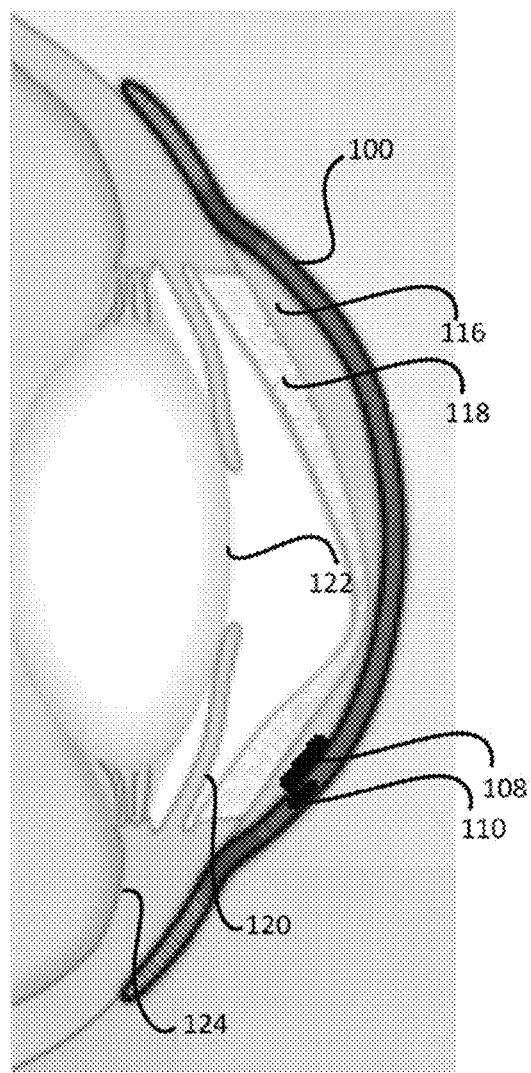
FIG. 11 shows a cross section view of the contact lens and the eye.

The contact lens 100 may have a diameter in a range of 15-24 mm, 17-22 mm, or 19-21 mm. A thickness of the contact lens 100 may be in a range of 0.1-0.5 mm, 0.2-0.4 mm, or about 0.3 mm. The thickness may be uniform throughout the lens. In some embodiments, the thickness tapers from the center of the contact lens 100 to the edge of the lens. In these embodiments, the thickness of the center may be in a range of 0.2-0.6 mm, 0.3-0.5 mm, or about 0.4 mm, and the thickness of the center may be in a range of 0.1-0.4 mm, 0.2-0.3 mm. Referring to FIG. 11, the contact lens 100 may rest on the sclera 124 and forms a vault over the cornea 118 (i.e., the contact lens 100 does not touch the cornea 118). The vault creates a tear reservoir 116 between the contact lens 100 and the eye. A distance between the eye and the concave surface of the contact lens 100 may be 20-400 µm, 50-300 µm, or 100-200 µm.

A tear is an aqueous fluid secreted from the lacrimal gland to coat the eye. The tear fluid is in contact with the blood supply through capillaries in the structure of the eye and includes many biomarkers found in blood that are analyzed to characterize a person's health condition(s). For example, the tear fluid includes glucose, calcium, magnesium, chloride, sodium, cholesterol, lactate, and potassium. The biomarker concentrations in the tear fluid can be systematically different than the corresponding concentrations of the biomarkers in the blood, but a relationship between the two concentration levels can be established to map tear film biomarker concentration values to blood concentration levels. For example, the tear fluid concentration of glucose can be established (e.g., empirically determined) to be approximately one tenth the corresponding blood glucose concentration. Although another ratio relationship and/or a non-ratio relationship may be used. Thus, measuring tear fluid analyte concentration levels provides a non-invasive technique for monitoring biomarker levels in comparison to blood sampling techniques performed by lancing a volume of blood to be analyzed outside a subject's body.

The contact lens 100 may be useful for monitoring tears glucose level in subjects with diabetes or subjects with prediabetes. Prediabetic subjects have a blood glucose level higher than normal but not high enough to be diabetic. For example, prediabetes subjects may have an level of hemoglobin A1c between 5.7-6.4% and/or a fasting blood glucose level of 100-125 mg/dl. The diabetes may be a polygenic form of diabetes (e.g., type 1 diabetes, type 2 diabetes), a monogenic form of diabetes (e.g., neonatal diabetes mellitus, maturity-onset diabetes of the young), or cystic fibrosis-related diabetes. The term "polygenic" refers to the risk of developing these forms of diabetes is related to multiple genes. The term "monogenic" refers to rare forms of diabetes result from mutations in a single gene. In subjects diagnosed with cystic fibrosis-related diabetes, a thick, sticky mucus that is characteristic of the disease causes scarring of the pancreas. This scarring may prevent the pancreas from producing enough insulin so the subjects become insulin deficient.

The photonic crystal 108 may be of any shape such as a circle, an oval, a triangle, a square, a rectangle, or a hexagon. The longest dimension measured from one end of the photonic crystal 108 to another end of the photonic crystal 108 may be in a range of 5-150 µm, 10-100 µm, 20-70 µm, or 30-50 µm. A thickness of the photonic crystal 108 may be in a range of 1-10 µm, 2-8 µm, or 3-5 µm. In some embodiments, the photonic crystal is a rectangle with a breadth in a range of 2-100 µm, 5-80 µm, 10-60 µm, or 20-40 µm.

The photonic crystal 108 may be disposed on the concave surface of the contact lens 100 such that the photonic crystal 108 is at least partially submerged in the tear reservoir 116 or in contact with the tear reservoir 116. Alternatively, the photonic crystal 108 may be embedded in the contact lens 100 and located near the concave surface of the contact lens 100. In most embodiments, the photonic crystal 108 may be disposed offset from the center of the eye so that the photonic crystal 108 does not interfere with the vision of the subject. For example, the photonic crystal may be positioned away from the pupil 122 and near a base of the iris 120 as shown in FIG. 11.

The photonic crystal 108 may be irreversibly attached to the contact lens 100 by placing the photonic crystal 108 in contact with the pre-polymerized contact lens mixture and then polymerizing the contact lens mixture thereby forming the contacts lens 100 which includes the photonic crystal 108. As used herein, "irreversibly attached" refers to the photonic crystal 108 being intimately joined to the concave surface of the contact lens 100 or being embedded in the contact lens, and the photonic crystal 108 cannot be detached from the contact lens 100 without damaging the photonic crystal 108, the contact lens 100, or both.

A porosity of the photonic crystal 108 may be at least 10 vol %, at least 20 vol %, at least 30 vol %, at least 40 vol %, or at least 50 vol %, and up to 80 vol %, or preferably up to 75 vol %, based on a total volume of the photonic crystal. In one embodiment, the porosity is calculated by taking a photograph of a cross section of the photonic crystal, measuring a total void area using the photograph, and calculating the porosity as a ratio of void area with respect to an entire cross sectional area of the photonic crystal. In this embodiment, the "areal" and "volumetric" porosities are equal for a porous media with a random structure. Alternatively, the porosity may be measured and/or calculated using $N_2$ adsorption/desorption isotherms (e.g., using Barret-Joyner-Halenda or non-local density functional theory), permporometry methods, industrial computed tomography scanning, and imbibition methods.

As used herein, the term "hydrogel" refers to a network of hydrophilic polymer chains dispersed in water. Hydrogels are absorbent natural or synthetic polymeric networks. Hydrogels also possess a degree of flexibility very similar to natural tissue, due to their significant water content.

The hydrogel may be a biocompatible material similar to those employed to form vision correction and/or cosmetic contact lenses in optometry. Exemplary natural polymers include, without limitation, agarose, methylcellulose, and hyaluronan. Exemplary synthetic polymers include, without limitation, silicone (e.g., dimethicone, methicone, phenyl trimethicone, and cyclomethicone), polyacrylamide, polymacon, polyethylene oxide, poly(2-acrylamido-2-methyl-1-propanesulfonic acid), polyvinylpyrrolidone, polyvinyl alcohol, sodium polyacrylate, poly(hydroxyethyl methacrylate), polymethacrylate, polyethylacrylate, polyethylene terephthalate, polymethyl methacrylate, and copolymers thereof.

In some embodiments, the synthetic polymer contains reacted monomers functionalized with boronic acid groups (e.g., alkylboronic acid and arylboronic acid). These monomers may be commercially available (e.g., 3-(acrylamido) phenylboronic acid, and 4-vinylphenylboronic acid) or synthesized according to methods known to one of ordinary skill in the art (G. Vancoilliea, R. Hoogenboom, Synthesis and polymerization of boronic acid containing monomers, Polymer Chemistry, 2016, 7, 5484-5495, incorporated herein by reference in its entirety). The boronic acid pendant groups may be useful for detecting the presence of analytes such as glucose.

In some embodiments, the synthetic polymer may include sensing groups in the polymer backbone. The sensing groups may be useful for detecting the presence of analytes. These groups include, without limitation, a cyclodextrin (e.g., α-cyclodextrin, β-cyclodextrin, and γ-cyclodextrin), a calixarene, a spirobifluorene, a macropolycyclic polyamide (e.g., octaamide) (X. Sun. T. D. James, Glucose sensing in supramolecular chemistry, Chem. Rev. 2015, 115, 8001-8037, incorporated herein by reference in its entirety).

The plurality of metal nanoparticle stacks are arranged within the hydrogel matrix. Each metal nanoparticle stack is defined as a region in the hydrogel matrix containing at least 70 vol %, 80 vol %, 90 vol %, or 95 vol % of metal nanoparticles relative to the total volume of the region (e.g., nanoparticle stack confine, see FIG. 1C). A width of each metal nanoparticle stack may be in a range of 10-50 nm, 12-25 nm, or 15-20 nm.

The plurality of metal nanoparticle stacks is spaced such that each metal nanoparticle stack is substantially parallel to one another. As used herein, the term "substantially parallel" refers to the metal nanoparticle stacks are separated by substantially the same distance. The metal nanoparticle stack may be aligned at no more than 5°, preferably no more than 3°, more preferably no more than 1°, relative to the adjacent metal nanoparticle stack.

The photonic crystal 108 is configured to shrink or swell in response to the concentration of an analyte. The distance between the adjacent metal nanoparticle stacks increases or decreases in response to a concentration of an analyte thereby producing a shift in a photonic band gap and a color change in the photonic crystal 108. The shift in the photonic band gap (and hence the change in the color) is reversible in that the photonic crystal functions even after swelling and shrinking for at least 10,000 times, 100,000 times, or 500,000 times. The position of the band gap and the color of the consequent resonant or reflected light may be controlled primarily by the spacing size between the metal nanoparticle stacks.

An initial thickness of the photonic crystal 108 may be in a range of 1-10 μm, 2-8 μm, or 3-5 μm, when the tears glucose level is in a normal healthy range of 10.16 mg/100 ml of tears. When the tears glucose level falls below 10 mg/100 ml, the photonic crystal may shrink and the thickness may be 0.7-9.5 μm, 1.4-7.6 μm, or 2.1-4.75 μm, and/or 70-95%, 80-90%, or 85-88% of the initial thickness. When the tears glucose level increases beyond 16 mg/100 ml, the photonic crystal may swell and the thickness may be 1.05-13.5 μm, 2.1-10.8 μm, or 3.15-6.75 μm, and/or 105-135%, 110-130%, or 120-125% of the initial thickness.

A distance between adjacent metal nanoparticle stacks is in a range of 140-250 nm. In some embodiments, the distance between adjacent metal nanoparticle stacks is 145-160 nm, or 148-150 nm. In these embodiments, the reflected light may be green or has a wavelength in a range of 450-500 nm, and the tears glucose level may be less than 10 mg/100 ml. In some embodiments, the distance between adjacent metal nanoparticle stacks is in a range of 170-200 nm, or 175-180 nm. In these embodiments, the reflected light may be yellow or has a wavelength in a range of 550-600 nm, and the tears glucose level is in a range of 10-16 mg/100 ml. In some embodiments, the distance between adjacent metal nanoparticle stacks is in a range of 205-240 nm, or 210-220 nm. In these embodiments, the reflected light may be red or has a wavelength in a range of 650-700 nm, and the tears glucose level is more than 16 mg/100 ml.

The efficiency of the photonic crystal in reflecting light may be affected by the number of metal nanoparticle stacks. For example, the efficiency may increase when there are more metal nanoparticle stacks. The photonic crystal may contain up to 30, 40, 50, 60, 70, 80, 90, or 100 metal nanoparticle stacks. In some embodiments, the photonic crystal contains 2-10, or 3-6 metal nanoparticle stacks.

The plurality of metal nanoparticle stacks may have a tilt angle in a range of 1-45°, 2-30°, 3-20°, or 4-6°. The tilt angle is measured from a plane of a metal nanoparticle stack to a plane parallel to a face of the photonic crystal (e.g., see FIG. 1C). While not wishing to be bound by theory, the reflected light may be more intense at a smaller tilt angle. In some embodiments, the tilt angle is more than 0° and up to than 1°, 0.1-0.8°, or 0.3-0.5°.

Each metal nanoparticle stack contains 20-200, 50-150, 80-120, 90-110, or 95-105 metal nanoparticles. The number of metal nanoparticles in each stack affects the amount of the reflected light. While not wishing to be bound by theory, the reflected light may be more intense when there are more metal nanoparticles in the stack. The metal nanoparticles may be randomly dispersed or evenly dispersed within each metal nanoparticle stack. The term "randomly dispersed" means the distance between a metal nanoparticle and all its neighbors are different. The term "evenly dispersed" means a distance between a metal nanoparticle and all its neighbors is the same or substantially the same. This distance can be said to be substantially the same when the shortest distance is at least 80%, at least 85%, at least 90%, or at least 95% of the average distance and the longest distance is not more than 120%, not more than 110%, or not more than 105% of the average distance. This distance may be measured from a center of a metal nanoparticle to another metal nanoparticle and may be in a range of 0.1 nm to 10 nm, 0.5-8 nm, 1-5 nm, or 2-3 nm. Energy-dispersive X-ray spectroscopy, X-ray microanalysis, elemental mapping, transmission electron microscopy, scanning electron microscopy, and scanning transmission electron microscopy may be useful techniques for observing the dispersion of the metal nanoparticles in each stack.

The metal nanoparticles contain silver, gold, titanium, platinum, iron, cobalt, chromium, molybdenum, vanadium, tin, nickel, niobium, alloys thereof, and mixtures thereof. Preferably, the metal nanoparticles contain silver. In some embodiments, the metal nanoparticles contain up to 50%, 60%, 70%, 80%, 90%, or preferably 100% of silver, based on a weight of the metal nanoparticles.

In preferred embodiments, the metal nanoparticles are spherical or substantially spherical (e.g., oval or oblong shape). In other embodiments, the metal nanoparticles may be of any shape that imparts desirable properties (e.g., high reflectance) to the photonic crystal. In some embodiments, the metal nanoparticles are in the form of at least one shape such as a rod, a cylinder, a rectangle, a triangle, a pentagon, a hexagon, a prism, a disk, a platelet, a flake, a cube, a cuboid, and an urchin (e.g., a globular particle possessing a spiky uneven surface).

In some embodiments, where the metal nanoparticles are spherical and consist of a noble metal (e.g., silver, gold, and platinum), the metal nanoparticles may be plasmonic nanoparticles. The electron density of the plasmonic nanoparticles may couple with the electromagnetic radiation of wavelengths that are far larger than the metal nanoparticle due to the nature of the dielectric-metal interface between the hydrogel and the metal nanoparticles.

The metal nanoparticles may be uniform. As used herein, the term "uniform" refers to no more than 10%, no more than 5%, no more than 4%, no more than 3%, no more than 2%, or no more than 1% of the distribution of the metal nanoparticles having a different shape. For example, the metal nanospheres are uniform and have no more than 1% of metal nanoparticles in an oblong shape. In some embodiments, the metal nanoparticles may be non-uniform. As used herein, the term "non-uniform" refers to more than 10% of the distribution of the metal nanoparticles having a different shape.

An average diameter of the metal nanoparticles may be in a range of 2-20 nm, 6-18 nm, or preferably 13-16 nm. In some embodiments, the metal nanoparticles have an average diameter in a range of 20-100 nm, 25-80 nm, 30-70 nm, 40-60 nm, or 45-55 nm. An average diameter, as used herein, refers to the average linear distance measured from a first point on the metal nanoparticle through the center of the nanoparticle to a second point directly across from the first point. While not wishing to be bound by theory, metal nanoparticles with a larger average diameter leads to a more intense reflected light.

The metal nanoparticles may not be agglomerated. Preferably, the metal nanoparticles are non-agglomerated (i.e. the metal nanoparticles are well separated from one another and do not form clusters). The metal nanoparticles may be crystalline, polycrystalline, nanocrystalline, or amorphous.

The metal nanoparticles in each stack may have a substantially uniform diameter (i.e., monodisperse). Dispersity is a measure of the heterogeneity of sizes of molecules or particles in a mixture. In probability theory and statistics, the coefficient of variation (CV), also known as relative standard deviation (RSD) is a standardized measure of dispersion of a probability distribution. It is expressed as a percentage and is defined as the ratio of the standard deviation ($\sigma$) of to the mean ($\mu$, or its absolute value $|\mu|$). The CV or RSD is widely used to express precision and repeatability. It shows the extent of variability in relation to the mean of a population. The metal nanoparticles having a narrow size dispersion, i.e. monodispersity, is preferred. As used herein, "monodisperse", "monodispersed" and/or "monodispersity" refers to metal nanoparticles having a CV or RSD of less than 25%, preferably less than 20%.

The metal nanoparticles may be monodisperse with a coefficient of variation or relative standard deviation (ratio of the particle size standard deviation to the particle size mean) of less than 15%, less than 12%, less than 10%, less than 9%, less than 8%, less than 7%, less than 6%, less than 5%, or preferably less than 2%.

In one embodiment, the metal nanoparticles are monodisperse and have a particle diameter distribution in a range of 75% of the average particle diameter to 125% of the average particle diameter, 80-120%, 85-115%, 86-114%, 87-113%, 88-112%, 89-111%, 90-110%, or preferably 95-105% of the average particle diameter.

In some embodiments, the average diameter of the metal nanoparticles varies between each metal nanoparticle stack. For example, the average diameter of the metal nanoparticles may increase by 0.1-3 nm, 0.3-2.5 nm, 0.5-2 nm, or preferably 1.3-1.6 nm from a metal nanoparticle stack nearest the cornea 118 to the metal nanoparticle stack furthest from the cornea 118.

In other embodiments, the average diameter of the metal nanoparticles is substantially the same for each metal nanoparticle stack.

The photonic crystal may be produced by methods known to those of ordinary skill in the art (A. K. Yetisen et al., Reusable, Robust and Accurate Laser-Generated Photonic Nanosensor, Nano Lett., 2014, 14 (6), pp 3587-3593, incorporated herein by reference in its entirety). For example, the hydrogel is formed by polymerizing the monomers. Subsequently, the hydrogel is perfused with an aqueous solution of the metal salt. Exemplary metal salts include, halides (e.g., fluoride, chloride, bromide, and iodide), nitrates, acetylacetonates, acetates, perchlorates, sulfamates, trifluoroacetylacetonates, carbonates, bicarbonates, methanesulfonates, ethanesulfonates, p-toluenesulfonates, salicylates, malates, maleates, succinates, tartrates, citrates, trifluoromethanesulfonates (triflates), hexafluorophosphates, hexafluoroacetylacetonates, sulfites, phosphate, and sulfates of silver, gold, titanium, platinum, iron, cobalt, chromium, molybdenum, vanadium, tin, nickel, and niobium. In most embodiments, the metal salt is a hydrate. Preferably, the metal salt is silver nitrate. The metal ions are reduced to metal nanoparticles in the hydrogel film. For example, silver ions are reduced to silver nanoparticles using a photographic developer. The hydrogel acts as a supporting medium for the embedded metal nanoparticles while also preventing agglomeration of metal nanoparticles.

The photonic crystal may be formed by photochemically patterning the hydrogel-metal nanoparticle system with a laser beam. Prior to exposure to the laser bean, the hydrogel containing the metal nanoparticles is backed by a mirror. An acute angle between the mirror and the hydrogel may be between 1-45°, 2-30°, 3-20°, or 4-6°. This acute angle directly correlates to the tilt angle of the metal nanoparticle stacks.

A wavelength, $\lambda$, of the laser may be in a range of 250-800 nm, 300-700 nm, or 400-600 nm. The standing waves of the laser allow the organization of the metal nanoparticles in regions where laser light beams may have constructively interfered, resulting in an ordered photonic structure with a periodicity of about $\lambda/2$ (e.g., 125-400 nm, 150-350 nm, or 200-300 nm). The periodicity also refers to the distance between the metal nanoparticle stacks. The laser may be directed at the hydrogel-metal nanoparticle system for 1-20 ns, 3-15 ns, or 5-10 ns thereby forming the photonic crystal.

The contact lens 100 may include a sensing platform to provide for continuous and automated monitoring of the analyte levels. The sensing platform includes an optical sensor 110, control electronics 112, and an antenna 114. The sensing platform may be situated on a substrate 104 embedded in the contact lens 100. The sensing platform may be embedded near the outer periphery of the contact lens 100 to avoid interference with incident light received closer to the central region of the cornea 118. Moreover, the substrate 104 may be formed of a transparent material to further mitigate effects on visual perception. A material is transparent when it transmits at least 70%, 80%, 90%, or 95% of the light it receives.

In some embodiments, the contact lens 100 does not have a sensing platform and the wearer may detect the glucose level is outside of the normal healthy range by observing the shade/color produced by the contact lens 100 (e.g., by looking into a mirror). For example, the photonic crystal turns green or blue when the glucose level is low and thus signals to the wearer to consume food.

The anterior layer 102 of the contact lens 100 may be greater than 30 µm, 40 µm, or 50 µm, and the posterior layer 106 of the contact lens 100 may be less than 170 µm, 160 µm, or 150 µm. In other embodiments, the sensing platform may be mounted on the inward-facing surface of the substrate 104 such that the sensing platform is facing the concave surface of the contact lens 100. The substrate 104 may be irreversibly attached to the anterior and posterior layers by adhesives, such as epoxy (e.g., bisphenol A epoxy, bisphenol F epoxy, glycidylamine epoxy, and novolac epoxy resin), silicone (e.g., polydimethylsiloxane and decamethyl cyclopentasiloxane), hot melt adhesives, ultraviolet light curing resins, visible light curing resins, moisture curing resins, and thermally curing resins.

The substrate 104 may be shaped as a disk or a ring (e.g., a disk with a centered hole). The substrate 104 may have a thickness sufficiently small to allow the substrate 104 to be embedded in the contact lens 100 without influencing the profile of the contact lens 100. The substrate 104 may have a thickness sufficiently large to provide structural stability suitable for supporting the electronics mounted thereon. For example, the substrate 104 may have a diameter of about 14-22 mm, 16-20, or 17-18 mm, and a thickness of 10-80 µm, 20-60 µm, or 30-50 µm. The substrate 104 may be a ring with a radial width sufficient to provide a mounting platform for the embedded electronics components. For example, the radial width may be 0.5-3 mm, 1-2 mm, or about 1.5 mm (e.g., an outer radius 0.5-3 mm, 1-2 mm, or about 1.5 mm larger than an inner radius).

The substrate 104 includes one or more surfaces suitable for mounting the control electronics 112, and the antenna 114. The substrate 104 may be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, substantially transparent conductive materials (e.g., indium tin oxide) may be patterned on the substrate 104 to form circuitry, electrodes, etc. For example, the antenna 114 may be formed by forming a pattern of gold or another conductive material on the substrate 104 by deposition, photolithography, electroplating, etc. Similarly, interconnects between the control electronics 112 and the antenna 114, and between the optical sensor 110 and the antenna 114, respectively, may be formed by depositing suitable patterns of conductive materials on the substrate 104. A combination of microfabrication techniques including, without limitation, the use of photoresists, masks, deposition techniques, and/or plating techniques may be employed to pattern materials on the substrate 104. The substrate 104 may be a relatively rigid material, such as polyethylene terephthalate ("PET") or another material configured to structurally support the circuitry and/or chip-based electronics within the contact lens 100. The contact lens 100 may alternatively be arranged with a group of unconnected substrates rather than a single substrate. For example, the control electronics 112 and the optical sensor 110 may be mounted to one substrate, while the antenna 114 is mounted to another substrate and the two may be electrically connected via the interconnects.

The optical sensor 110 detects the color of the light reflected from the photonic crystal 108 and feedbacks to the control electronics 112 which transmits the data to an external device. The optical sensor 110 may be positioned on the substrate to receive at least part of the reflected light from the photonic crystal 108. For example, the optical sensor 110 may be arranged on the substrate to face inward, toward the corneal 118 surface, so as to detect the light reflected from the photonic crystal 108. The optical sensor 110 may generate an output signal indicative of a concentration of an analyte that diffuses through the photonic crystal 108. The sensor may monitor the level of the analyte (e.g. glucose) automatically and/or throughout the day (e.g., every 1-60 minutes, 2-40 minutes, or 5-10 minutes). The sensor may be a photoconductive sensor or a photodiode. The sensor may be powered by a battery (rechargeable or non-rechargeable) or external radio frequency sources (Young, D. J. et al., Lab Chip, 2015, 15, 4338-4347—incorporated herein by reference in its entirety). For example, the optical sensor 110 of the sensing platform may be configured with, or be part of, a radio frequency identification (RFID) tag. The RFID tag and device may communicate using an RFID protocol (e.g., an RFID generation 2 protocol). The RFID tag may be configured to receive radio signals from the device. In some embodiments, the device's signals may be used for both communicating with and powering the RFID tag. In other embodiments, the RFID tag may be a powered device (e.g., be configured with a battery that powers the tag).

The optical sensor 110 may be configured to detect the light reflected from the photonic crystal 108 while being worn in an eye of a wearer (i.e., subject). The optical sensor 110 may store data (e.g., wavelength) related to the reflected light, and subsequently send the data upon request from the device. The device, in turn, may store and/or process the received data. For example, the device may process the wavelength data to determine analyte-related information about the wearer.

The optical sensor 110 may be irreversibly attached to the substrate 104 by adhesives, such as epoxy (e.g., bisphenol A epoxy, bisphenol F epoxy, glycidylamine epoxy, and novolac epoxy resin), silicone (e.g., polydimethylsiloxane and decamethyl cyclopentasiloxane), hot melt adhesives, ultraviolet light curing resins, visible light curing resins, moisture curing resins, and thermally curing resins.

The external device may radiate radio frequency radiation to power the optical sensor 110 and/or the sensing platform. The device may thereby control the operation of the sensing platform by controlling the supply of power to the sensing platform. In some examples, the device may operate to intermittently power the sensing platform to provide a reading by radiating sufficient radiation to power the sensing platform to obtain a measurement and communicate the result. The device may also store the sensor results communicated by the sensing platform. In this way, the device may acquire a series of analyte concentration measurements over time without continuously powering the sensing platform.

The device may be, for example, a wearable device (e.g., a watch, a wristband, or a head-mountable display), a laptop, a desktop, a handheld or tablet computer, a mobile phone, or a subsystem of such a device. The device may include a processing system; e.g., a central processing unit (CPU), and a non-transitory computer readable medium configured to store at least program instructions. The device may store the data received from the sensing platform, process the data, and generate display(s) based on the received and/or processed data.

In some embodiments, the device may be configured with configuration data to perform glucose-related processing. For example, the device may include configuration data such as wavelength data for various levels of glucose concentration. Based on this configuration data, the device may determine a tears glucose concentration for the wearer. Also, the wearer may provide blood glucose concentration(s) and corresponding tears glucose concentration(s) for the wearer to the device (for example, during configuration), and the display device may determine relationships between blood glucose concentration(s) and tears glucose concentration(s).

Figure 12:
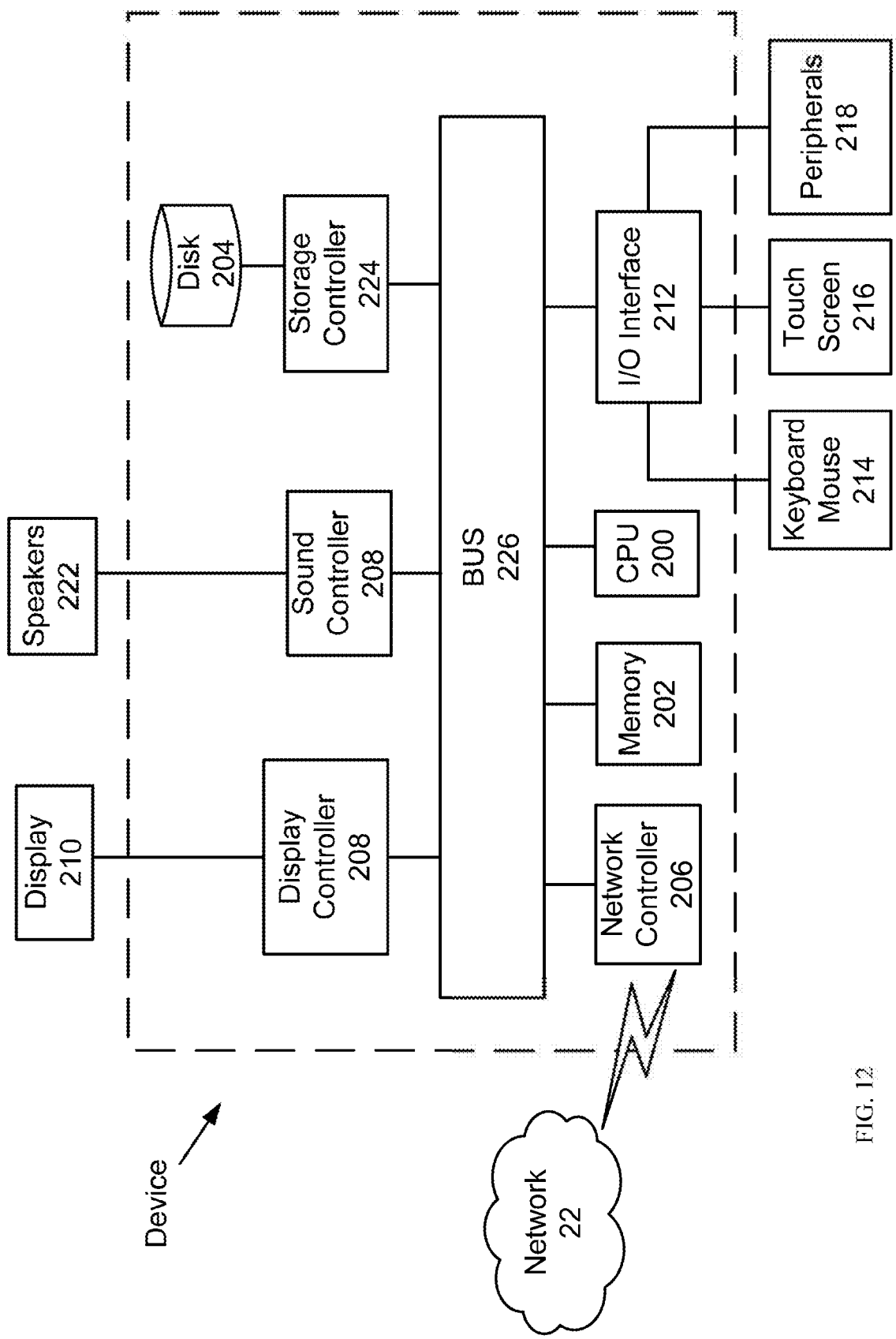
FIG. 12 is a diagram of an embodiment of the device.

A hardware description of the device according to exemplary embodiments is described with reference to FIG. 12. In FIG. 12, the device includes a CPU 200 which performs the processes described above. The process data and instructions may be stored in memory 202. These processes and instructions may also be stored on a storage medium disk 204 such as a hard drive (HDD) or portable storage medium or may be stored remotely. Further, the present disclosure is not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the device communicates, such as a server or computer.

Further, the device may be provided as a utility application, background daemon, or component of an operating system, or combination thereof, executing in conjunction with CPU 200 and an operating system such as Microsoft Windows 7, UNIX, Solaris, LINUX, Apple MAC-OS and other systems known to those skilled in the art.

The hardware elements in order to achieve the device may be realized by various circuitry elements, known to those skilled in the art. For example, CPU 200 may be a Xenon or Core processor from Intel of America or an Opteron processor from AMD of America, or may be other processor types that would be recognized by one of ordinary skill in the art. Alternatively, the CPU 200 may be implemented on an FPGA, ASIC, PLD or using discrete logic circuits, as one of ordinary skill in the art would recognize. Further, CPU 200 may be implemented as multiple processors cooperatively working in parallel to perform the instructions of the inventive processes described above.

The device in FIG. 12 also includes a network controller 206, such as an Intel Ethernet PRO network interface card from Intel Corporation of America, for interfacing with network 22. As can be appreciated, the network 22 can be a public network, such as the Internet, or a private network such as an LAN or WAN network, or any combination thereof and can also include PSTN or ISDN sub-networks. The network 22 can also be wired, such as an Ethernet network, or can be wireless such as a cellular network including EDGE, 3G and 4G wireless cellular systems. The wireless network can also be WiFi, Bluetooth, or any other wireless form of communication that is known.

The device further includes a display controller 208, such as a NVIDIA GeForce GT2 or Quadro graphics adaptor from NVIDIA Corporation of America for interfacing with display 210, such as a Hewlett Packard HPL2445w LCD monitor. A general purpose I/O interface 212 interfaces with a keyboard and/or mouse 214 as well as a touch screen panel 216 on or separate from display 210. General purpose I/O interface also connects to a variety of peripherals 218 including printers and scanners, such as an OfficeJet or DeskJet from Hewlett Packard.

A sound controller 220 is also provided in the device, such as Sound Blaster X-Fi Titanium from Creative, to interface with speakers/microphone 222 thereby providing sounds and/or music.

The general purpose storage controller 224 connects the storage medium disk 204 with communication bus 226, which may be an ISA, EISA, VESA, PCI, or similar, for interconnecting all of the components of the device. A description of the general features and functionality of the display 210, keyboard and/or mouse 214, as well as the display controller 208, storage controller 224, network controller 206, sound controller 220, and general purpose I/O interface 212 is omitted herein for brevity as these features are known.

Example 1 Design of the Photonic Crystal Using Computer Simulation

Figure 1A:
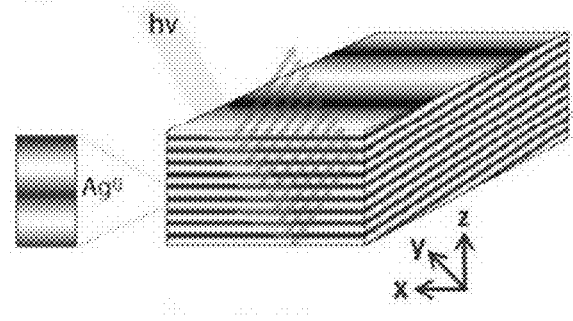
FIG. 1A is a schematic of the 1D photonic crystal in a contracted state.
Figure 1B:
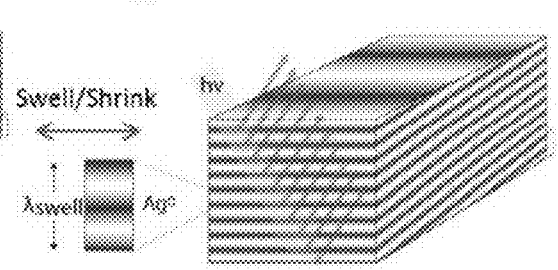
FIG. 1B is a schematic of the 1D photonic crystal in a swollen state.

The photonic crystal that is analyzed consisted of silver nanoparticles which are embedded in poly(hydroxyethyl methacrylate) (pHEMA) hydrogel (see FIGS. 1A and 1B). A series of simulations were performed using the finite element method to study the efficiency, performance, tunability of photonic crystals (Bragg mirror sensors) with a 5° slanted lattice akin to blazed transmission gratings.

Two-dimensional (2D) modeling of the photonic crystal sensor was achieved using finite element analysis, COMSOL Multiphysics®. This software was used in conjunction with MATLAB in order to generate the nanoparticle-based structures, which were utilized to simulate different model geometries. A MATLAB code was written to enable the construction of the 1D photonic crystal sensor. The code was set up to generate randomly sized nanospheres distributed within periodic layers. The nanospheres' positions within the layers were defined such that vertically they were normally distributed but in the horizontal axis, position was given by a normal random distribution where the average position was fixed at a distance equivalent to the lattice constant. The nanospheres therefore were effectively forced to take a position within a rectangular domain (layers), defined by these conditions (see FIG. 1c). The radii of the nanospheres (representative of silver nanoparticles) followed a normal random distribution to mimic fabricated devices (Yetisen A K et al. (2015) Photonic nanosensor for colorimetric detection of metal ions. Anal Chem 87(10): 5101-8, incorporated herein by reference in its entirety).

The code allowed for the control of the average radius of the nanospheres where the initial run used a value of radius r=9 nm with a standard deviation of 2 nm. The wavelength was selected to reflect $\lambda=450$ nm at its maxima and refractive index of the hydrogel medium was set to n=1.512. This allowed for the calculation of the lattice constant, l, where $l=\lambda/2n$. Other controllable parameters included number of nanospheres within each stack and number of stacks.

The generated nanoparticle structures were then imported into COMSOL, rotated by 5° anticlockwise and then enclosed by a square computational domain (see FIGS. 1A-1D). A cross-section of the photonic crystal structure is shown in FIGS. 1A-1B. The overall geometry had a stack of layers arranged periodically only in the z-direction. The layers extend in the x-y directions; hence, a 2D cross-section model was a reasonable simulation geometry of the photonic crystal. Although 3D simulation may be more accurate, it requires more time and computational capabilities.

Figure 1C:
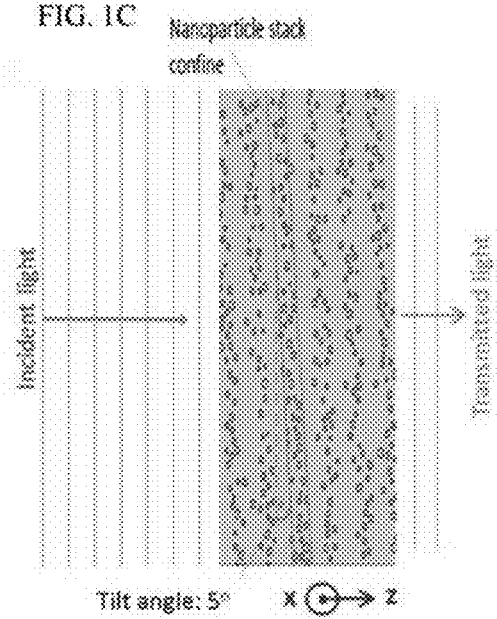
FIG. 1C shows the geometry of a photonic crystal with 6 metal nanoparticle stacks.
Figure 1D:
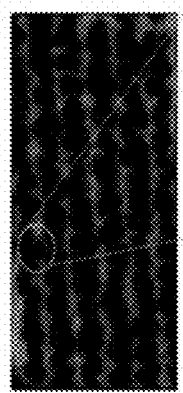
FIG. 1D shows the associated mesh and finite elements.
Figure 1E:
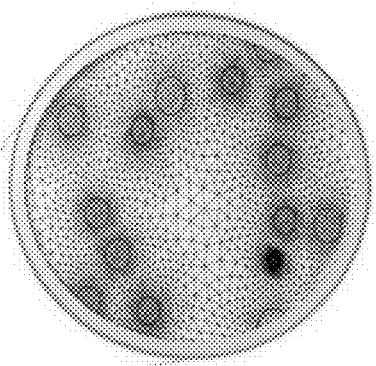
FIG. 1E is an expanded view of the mesh and finite elements.

Using the Drude model of permittivity, the refractive index of silver nanoparticles was modeled where both real and imaginary components were provided and assigned to the nanosphere domains (Palik E D (1984) Handbook of optical-constants. J Opt Soc Am A Opt Image Sci Vis 1(12):1297-1297, incorporated herein by reference in its entirety). Following the addition of the material properties, scattering boundary conditions were applied around the crystal. FIG. 1C shows the entry line for electromagnetic waves moving incident on the crystal from left to right through the stacks of nanospheres. A mesh size defined by COMSOL as "finer" was used throughout, possessing an average element size of roughly 5 nm (FIG. 1D). This structure was then studied with a parametric sweep, allowing a range of wavelengths (400-900 nm) to be solved in a single run of a simulation, with a 5 nm step size. Boundary integration was performed on the right hand boundary, inspecting "power outflow, time average", to obtain the plots for a power transmissions against wavelengths. The transmission spectra were normalized by dividing with peak intensity. The simulation process was repeated for six sets of geometries and the transmission spectra were plotted. Throughout the six simulations, there were three key changes in performance of the photonic crystal although each crystal did not necessarily all exhibit the three changes. These changes consisted of an induced red shift, a wider band gap, and also the level of normalized transmission increased in some cases, in turn reducing the peak reflectivity.

All of the simulations were performed with the lattice angled at 5° from the surface plane of the photonic crystal. The comparative effect of having this lattice arrangement was negligible to having the lattice parallel to the long sides. With no noticeable tainting in efficiency or performance between these two configurations, the 5° tilt offered a reasonably efficient configuration. Without the tilted lattice, the photonic crystal has no practical applications because the diffracted light interferes with the incident light.

The swelling of hydrogel matrix was reported to occur in response to analytes (pH, metal ions, glucose) (Yetisen A K et al. (2014) Pulsed laser writing of holographic nanosensors. J Mater Chem C 2(18):3569-3576; Yetisen A K (2015) Holographic Glucose Sensors, in Holographic Sensors. Springer International Publishing, p. 101-134; Yetisen A K et al. (2014) Holographic sensors: three-dimensional analyte-sensitive nanostructures and their applications. Chem Rev 114(20): 10654-10696; and Yetisen A K (2015) Holographic pH Sensors, in Holographic Sensors. Springer. p. 53-83, each incorporated herein by reference in their entirety). The swelling not only increased the distance between the nanoparticle layers but also changed the refractive index of the hydrogel. To keep the findings more generic, the variation in refractive index was not considered in this work. Rather, the focus was on the optical effects related to the organization of nanoparticles. The refractive index of the hydrogel depends on many factors such as polymer type, molecular weight of the polymer, the concentration of the crosslinker, functional groups, and the concentration-dependent refractive index of the analyte. In this disclosure, a constant index of refraction, and constant temperature and humidity conditions were considered in the simulations.

Example 2 Lattice Spacing Size

Figure 2A:
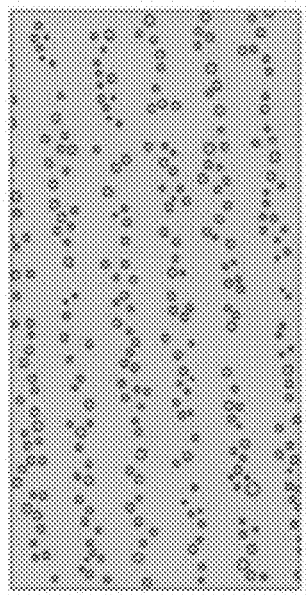
FIG. 2A shows the geometry of a photonic crystal with a distance of 149 nm between each metal nanoparticle stack.
Figure 2B:
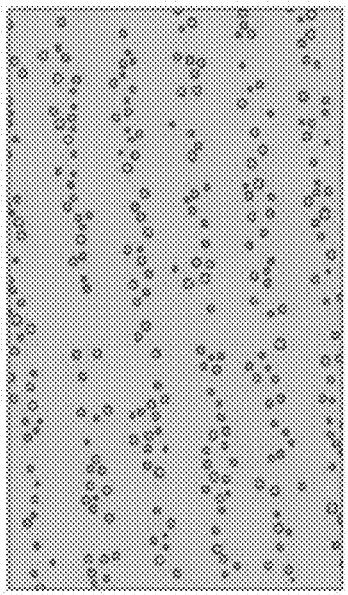
FIG. 2B shows the geometry of a photonic crystal with a distance of 175 nm between each metal nanoparticle stack.
Figure 2C:
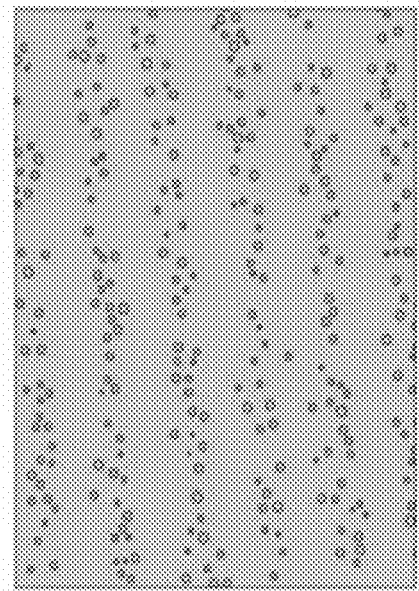
FIG. 2C shows the geometry of a photonic crystal with a distance of 215 nm between each metal nanoparticle stack.
Figure 2D:
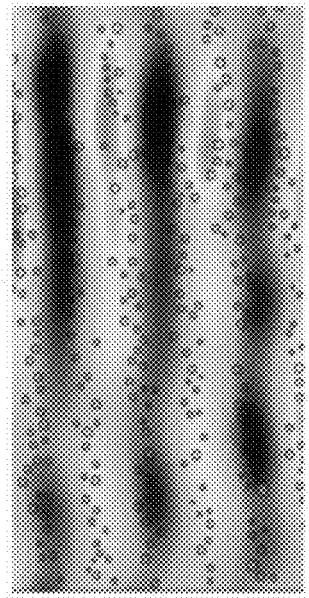
FIG. 2D is an electric field plot of propagating electromagnetic waves (wavelength of 450 nm) in the photonic crystal shown in FIG. 2A.
Figure 2E:
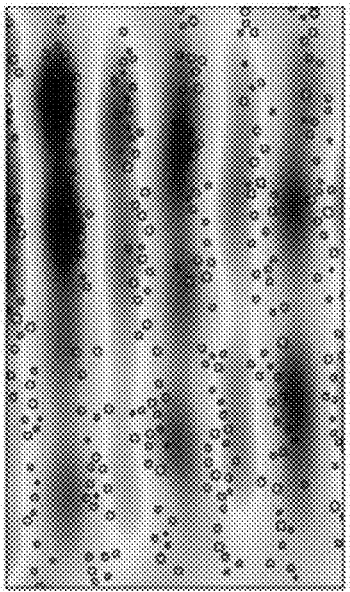
FIG. 2E is an electric field plot of propagating electromagnetic waves (wavelength of 530 nm) in the photonic crystal shown in FIG. 2B.
Figure 2F:
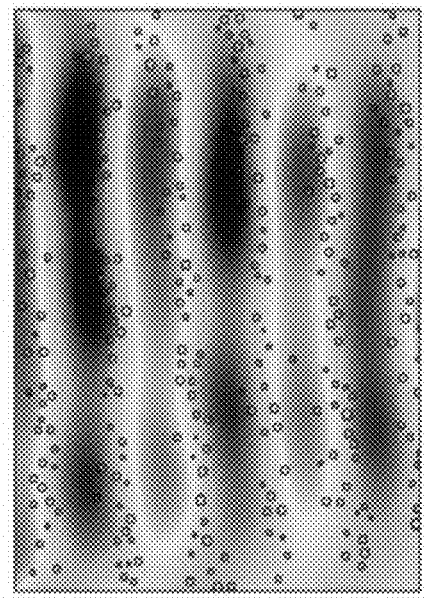
FIG. 2F is an electric field plot of propagating electromagnetic waves (wavelength of 650 nm) in the photonic crystal shown in FIG. 2C.
Figure 2G:
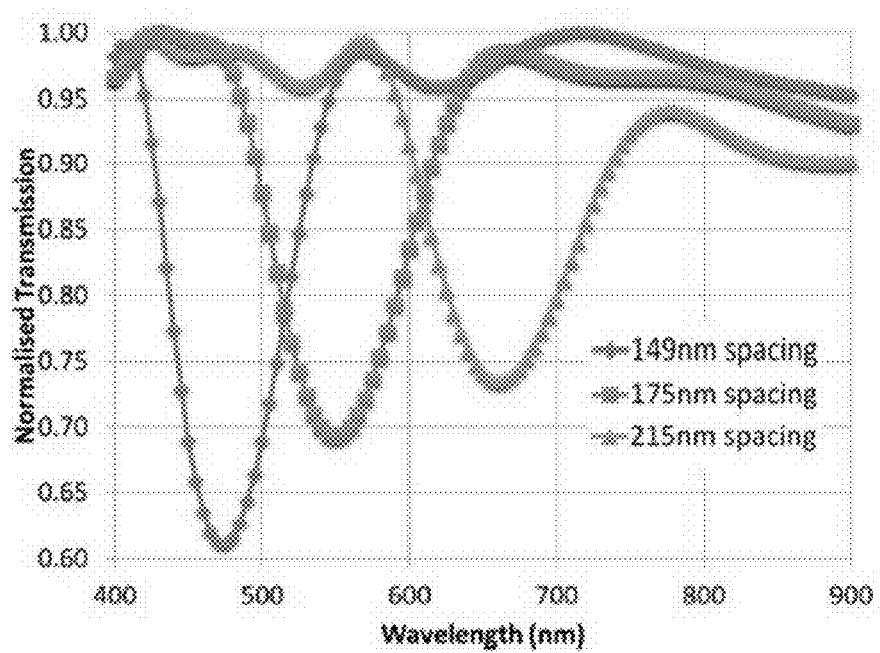
FIG. 2G is an overlay of the transmission spectra for photonic crystals with different lattice spacing.

The effective distance between each stack of the lattice was investigated. The number of stacks was set to six, there were 50 particles in each stack, and the particles had an average radius of 9 nm. The wavelengths that should exhibit the most reflection (governing the spacing size) were $\lambda=450$ nm, 530 nm, and 650 nm. These also equated to corresponding lattice constants (l) shown in FIG. 2G. The geometries used in the simulation are shown in FIGS. 2A-2C and coupled with them are their respective electric field plots (see FIGS. 2D-2F). In the electric field plots, the red wave fronts represent maximum power and the dark blue a minimum. The spacing size between the nanoparticle stacks increased from FIGS. 2A and 2D through to FIGS. 2C and 2F. The associated transmission spectrum is illustrated in FIG. 2G. Minimum transmission and peak reflectivity of the photonic crystal were located at the minimum point of the dip of each curve where $\lambda \approx 450$ nm for a lattice spacing size of 149 nm. Similarly the minimum point appeared at around $\lambda=530$ nm for the middle spacing size of 175 nm and at $\lambda=\sim650$ nm for 215 nm spacing. The minimum points should fall at the relevant resonant wavelength, but the above results showed a consistent deviation (from expected 450 nm, 530 nm, 650 nm) of about 20 nm toward longer wavelengths. The dip represents the band gap and its position translates to the modes of light that are reflected (e.g., not "allowed" through the crystal). In the case of 149 nm lattice spacing, the modes of light were removed around the 530 nm wavelength to reflect green. As the lattice spacing increased, the band gap shifted toward longer wavelengths.

In order to understand the red shift of the band gap, it must be noted that the whole photonic crystal was expanding as the spacing size increased. The position of the band gap is directly linked to the distance the wave has to travel through the multilayer structure. The band gap appeared when returning (reflected) waves destructively interfere with incoming waves thus eliminating a specific set of wavelengths (or modes), called a band gap. If the waves had to travel further, the position at which this band appeared would shift upwards. The band gap also experienced a decreased contrast in transmission, as the peak became shallower. The transmission was directly linked to the efficiency of the structure, and so it can also be said that as the lattice expanded, the efficiency decreased. This observation may be due to the changing effective refractive index between the stacks and the medium. As the photonic crystal expanded, the density of particles within each stack decreased, which reduced the effective refractive index of the stack. As this effective refractive index decreased so too does the depth of the band gap and the efficiency of the crystal. This observation is elaborated in the subsequent sections.

Example 3 Average Nanoparticle Size

The mean size of the nanospheres within the stacks was investigated. The spacing size remained constant at l=175 nm (suggesting the presence of the band gap at $\lambda=530$ nm) as well as the number of stacks (i.e., 6) with 60 particles per stack. The average sizes to be tested ranged from 6 nm to 16 nm at a 2 nm interval. The six required geometries were constructed with parameters listed in "Lattice Spacing Size" section. FIG. 3 shows the transmission spectrum and the depth of the dip (representing the intensity of the reflection band) increased as the average particles size increased. The increase in average particle size resulted in increased intensity and band gap width, as well as a red shift. This effect can be explained by the scattering from silver nanoparticles. As the average nanoparticle size increased, the plasmonic resonance peak red shifted and so did the scattering peaks. This phenomenon was observed in the form of the broad and low transmission (dips) (Liu Z et al. (1998) Red shift of plasmon resonance frequency due to the interacting Ag nanoparticles embedded in single crystal $SiO_2$ by implantation. Appl Phys Lett 72(15):1823-1825; and Zhao Y, Deng Z-q, Li J (2014) Photonic crystal fiber based surface plasmon resonance chemical sensors. Sensors Actuators B Chem 202:557-567, each incorporated herein by reference in their entirety).

Figure 3A:
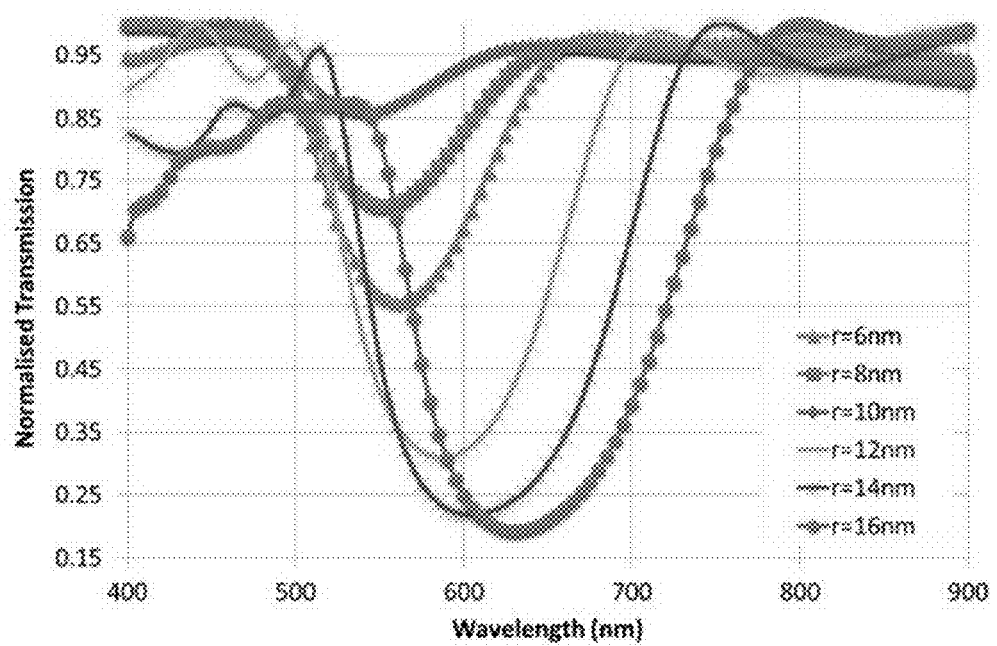
FIG. 3A is an overlay of the transmission spectra for photonic crystals with different sizes of metal nanoparticles.
Figure 3B:
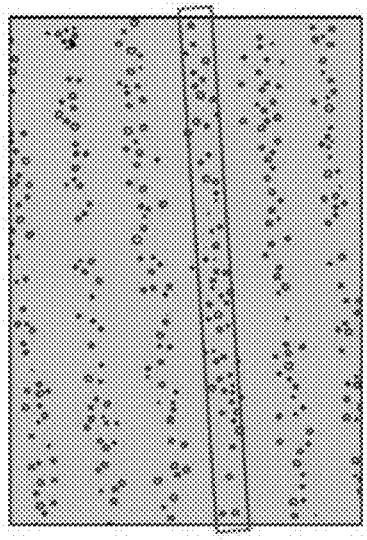
FIG. 3B shows the geometry of a photonic crystal with an average metal nanoparticle size of 6 nm.
Figure 3C:
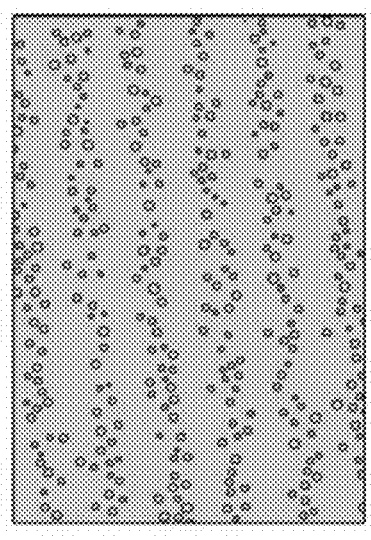
FIG. 3C shows the geometry of a photonic crystal with an average metal nanoparticle size of 10 nm.
Figure 3D:
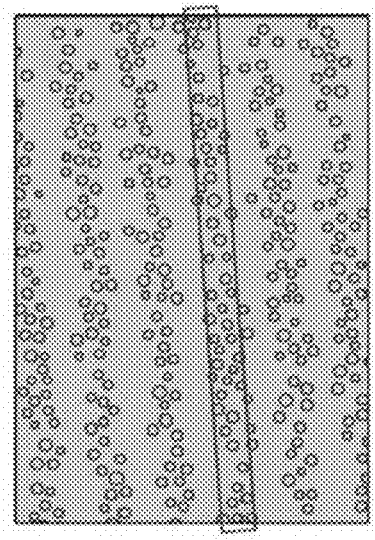
FIG. 3D shows the geometry of a photonic crystal with an average nanoparticle size of 14 nm.

The broadened band gap may also be due to the operating principle of the MATLAB code because the centers (not the perimeters) of the particles were confined to the stacks by a rectangle of fixed size. As the particle size increased, the code had to compute positions to fit all the particle's centers within this same rectangle. This effect was two-fold; the effective refractive increased since a larger area of the stack was filled with particles (rather than the hydrogel matrix), and also that the effective spacing size between the stacks decreased, as sections of the particles existed outside of the rectangle (FIG. 3D). In this example, the lattice remained a fixed size and as the particles became larger, more area within the stack was filled. This caused an effective elevation of dielectric contrast and effective refractive index, increasing the intensity. FIG. 3D shows the structure where the average particle size was large. There was little uniformity in the width of each stack. This incurred a slightly different spacing size between each stack and consequently introduced a number of band gaps. These band gaps were of similar coverage and overlap resulting in one gap of large bandwidth. Bandwidth was also narrowed by increasing the particle density.

Example 4 the Number of Nanoparticles Per Stack

Figure 4:
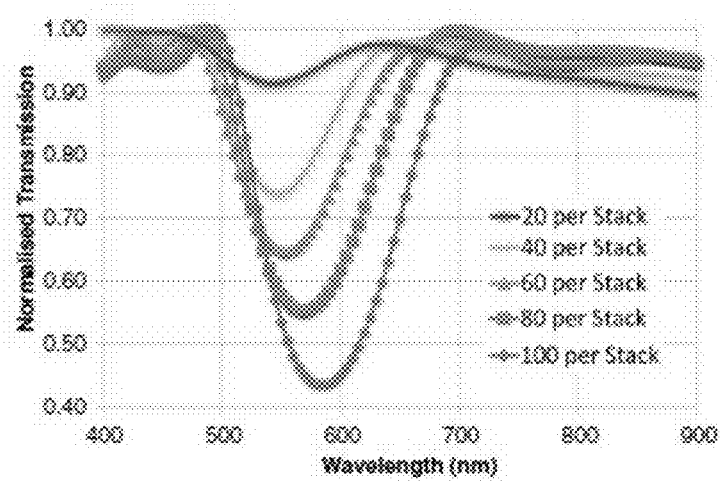
FIG. 4 is an overlay of the transmission spectra for photonic crystals with different number of metal nanoparticles in each stack.

The effect of increasing number of particles in each layer was also evaluated. Five geometries were constructed with 6 stacks and an average particle size of 9 nm. A lattice constant of l=175 nm was utilized. Initially, there were 20 particles per layer, increasing by 20 each time up to 100 (FIG. 4).

With a growth in the number of particles per layer, the band gap deepened, showing an increased reflectivity. There was, however, a slight red shift present with increasing particles in the stacks. The trough of each transmission curve widened as the stacks are filled with more particles. Adding more nanoparticles to the layers increased the surface coverage of the stack. In covering more of the stack, there was improved uniformity. The effective refractive index contrast sharpened, justifying the stronger reflection band. With a relatively empty configuration of 20 particles per stack, there was a 10% difference in reflectivity between the stop band and the maximum. In comparison, when the stack was filled up with 100 particles, this value reaches 65%. The slight red shift can also be accounted for the tighter proximity (or increased density) of nanoparticles increasing plasmonic resonance. The silver nanoparticles had strong absorption and scattering qualities as accounted for by the complex refractive index. The increase in the number of the particles increased the absorptive surface area and scattering, which results in lower light transmission.

Example 5 Number of Stacks

The number of nanoparticle stacks in the photonic crystal was investigated. Most of the parameters were fixed with the values seen previously, whereby the lattice constant was l=175 nm, the mean particle size was r=9 nm and there were 50 particles per stack. The number of layers was varied from 3 to 6.

Figure 5:
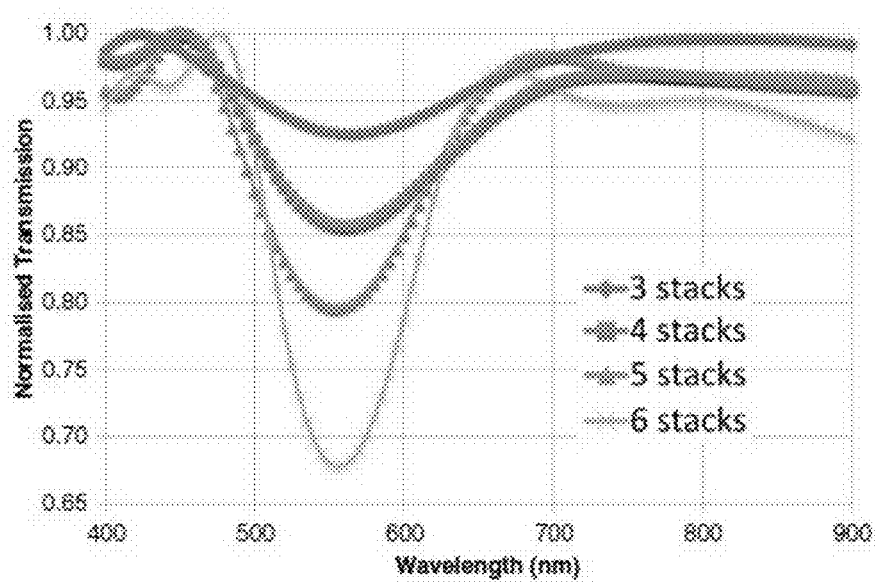
FIG. 5 is an overlay of the transmission spectra for photonic crystals with different number of stacks.

FIG. 5 shows the different transmission responses to an increasing number of layers within the photonic crystal. As the number of layers (or stacks) increased, a narrower and more intense band gap was observed. With 6 stacks, there was a 70% transmission leading to near 30% reflectivity, whereas the photonic crystal with 5 stacks showed an 80% transmission and 20% reflectivity. There was a consistent band gap positioning in regard to the position on the visible light spectrum ($\lambda \approx 530$ nm). There was a consistent deviation from the expected position of the band gap by 20 nm, in the same direction as shown in FIGS. 3 and 4. Having more stacks resulted in stronger reflectivity and a slight narrowing of the band gap width. While the periodicity stayed constant, the entirety of the structures broadened with added stacks. The incident waves would come into contact with more reflected waves and hence a higher level of destructive interference would be exhibited thus improving reflectivity.

Example 6 Increasing the Average Size of Particles Across Stacks

Figure 6A:
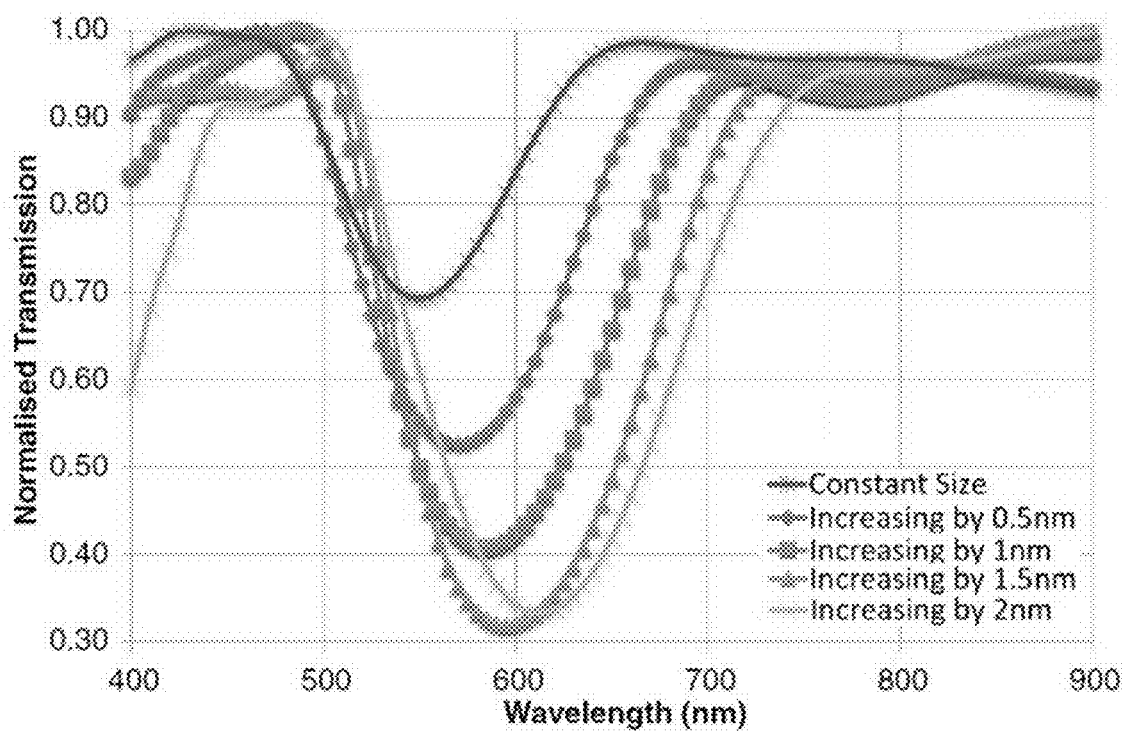
FIG. 6A is an overlay of the transmission spectra for photonic crystals with an increasing average particle size across stacks.
Figure 6B:
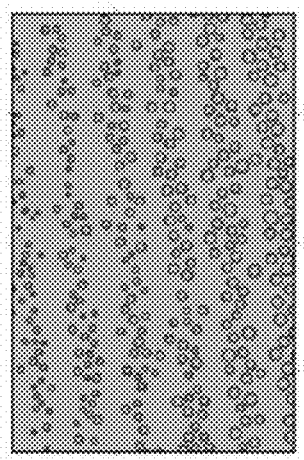
FIG. 6B shows the geometry of a photonic crystal with an increasing average particle size by 2 nm per stack.

The variation in particle size meant that there could be potential anomalies in the structures. For example, an anomaly was observed when nanoparticle size increased across the crystal. This was encountered in the fabrication of the crystal whereby an inhomogeneous distribution of particles was obtained due to the uneven reduction of $Ag^+$ ions to $Ag^0$ nanoparticles using a photographic developer. FIG. 6B shows a photonic crystal where the mean particle size ranged from 9 to 19 nm.

To simulate this, a standard configuration was applied (see FIGS. 2A-2C), using a lattice constant of l=175 nm, but there was an increasing average particle size from one stack to another. The first spectrum was plotted whereby the average particle size started at 9 nm and increased by 0.5 nm from left to right. FIG. 6A shows a sample geometry of 2 nm increments. The stack on the far left hand side had an average particle size of 9 nm, the second one across had an average particle size of 11 nm, and the middle stack had an average particle size of 13 m.

The transmission spectra seen in FIG. 6A had many similarities with FIG. 5. As the stacks became larger incrementally, the band gap positions dropped, as in all cases. There was a slight red shift from the constant size to the 1.5 nm increase, but between the last two cases there was a higher shift. As particle size became larger (i.e., had a wider width), the spacing between the stacks decreased. The combination of the larger lattice constant and the lack of consistency between spacing sizes accounted for the increased band gap width. The red shift between the 1.5 nm and 2.0 nm particle spectra was likely caused by increased plasmonic resonance/scattering due to the increase in particle size and density. Although the reflectivity was larger when the increment was 2 nm, the broadness of the band reduced the crystal's ability to exhibit a selective light reflection.

Example 7 Defect Effects

Figure 7A:
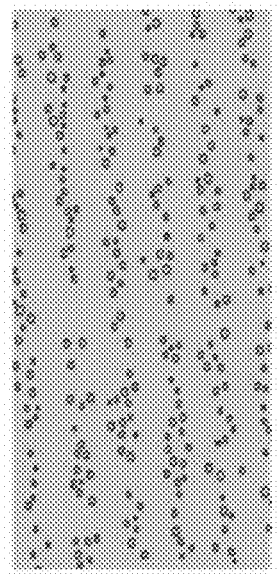
FIG. 7A shows the geometry of a photonic crystal without defect and has an inter-stack spacing of 175 nm.
Figure 7B:
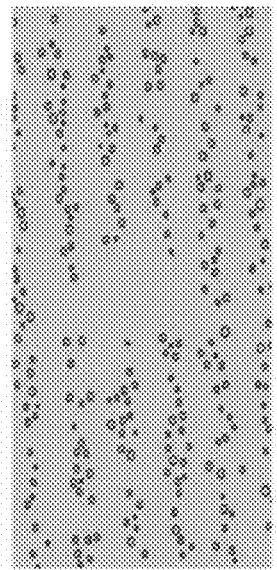
FIG. 7B shows the geometry of a photonic crystal with a defect and has an inter-stack spacing of 175 nm.
Figure 7C:
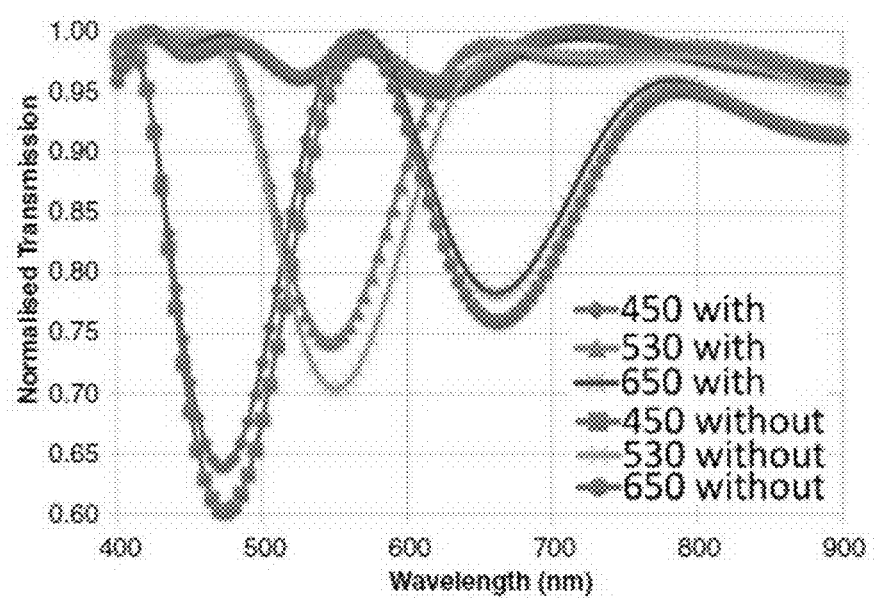
FIG. 7C is an overlay of the transmission spectra for photonic crystals with and without a defect and has different spacing size (nm).

Another anomaly is a defect. A defect was introduced into the simulation of increasing spacing size (see. FIG. 2G) in the form of an empty region in the centre of the lattice (see FIGS. 7A-B). The empty region had the same refractive index as the hydrogel medium. The introduction of a defect into the photonic crystal decreased the normalised transmission in the band gap (see FIG. 7C). This could be due to the increased random scattering from the defect. Light was scattered in all directions and less light was transmitted in the normal propagation direction.

Example 8 Varying the Tilt Angle

Simulations were performed to understand the effect of increasing the lattice tilt angle on the performance and efficiency of the photonic crystal. Thus far, the 5° tilt angle did not show a real difference in performance (barring the slight error in the dip position). A photonic crystal was generated that could be rotated while maintaining key geometrical properties. The MATLAB code was modified such that it produced a structure with many layers and of excess height but with a standard 9 nm average nanoparticle radius and a lattice constant of l=175 nm. A graphic illustration of why the excess height was needed can be seen in FIG. 8A. Empty spaces would be left if the regular structure was used (see FIG. 8B). By using this technique, a consistency in geometries was obtained. These geometries were tested in the same manner as before and produced a complex set of results.

FIG. 8C suggests that a more obtuse slant in the lattice should result in a blue shift and should reduce the intensity. Previous findings suggested that rather a red shift should be experienced. As the lattice rotated relative to the centre of the photonic crystal, the effective spacing and distance that the plane wave travels increased. However, the response was the opposite. One possible reason for the blue shift can be that as the tilt angle increased the layers of nanoparticles no longer act as a photonic crystal but rather act as a blazed grating. This grating may have reflected the wavelengths according to title angles rather than lattice spacings. The intensity decreased and matched with the theory that as the spacing grew the intensity decreased. It was anticipated that the slant angle would account for the slight discrepancy in the position of the band gap from the expected in FIG. 8C. There was a consistent red shift of 20 nm from the projected position of the band gap. FIG. 8C shows that no shift in band gap position was experienced between 0° and 5° slants. The discrepancy may be accounted for as a systematic error in the generation of the structure in MATLAB. The code used to determine the lattice spacing (affecting band gap position) may not yield a precise mesh. The consistency of the error suggested that it should be almost neglected and the band gap positions can be assumed to be in the correct position (20 nm towards the blue end of the spectrum).

Figure 9A:
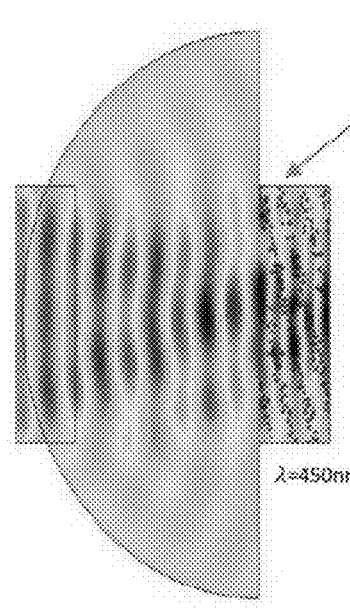
FIG. 9A is an electric field plot of propagating electromagnetic waves (wavelength of 450 nm) for a photonic crystal with a 15° tilt angle.
Figure 9B:
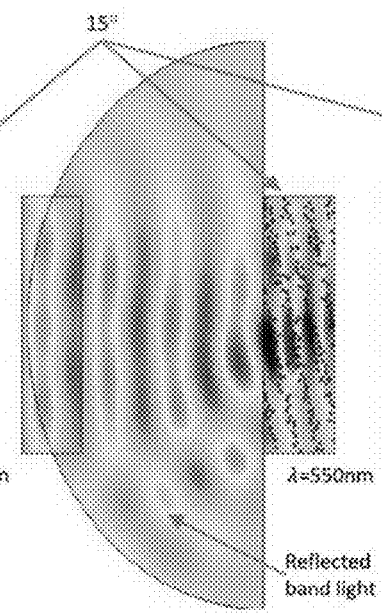
FIG. 9B is an electric field plot of propagating electromagnetic waves (wavelength of 550 nm) for a photonic crystal with a 15° tilt angle.
Figure 9C:
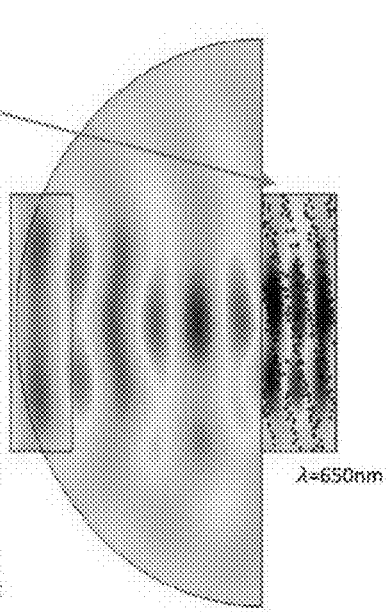
FIG. 9C is an electric field plot of propagating electromagnetic waves (wavelength of 650 nm) for a photonic crystal with a 15° tilt angle.
Figure 10:
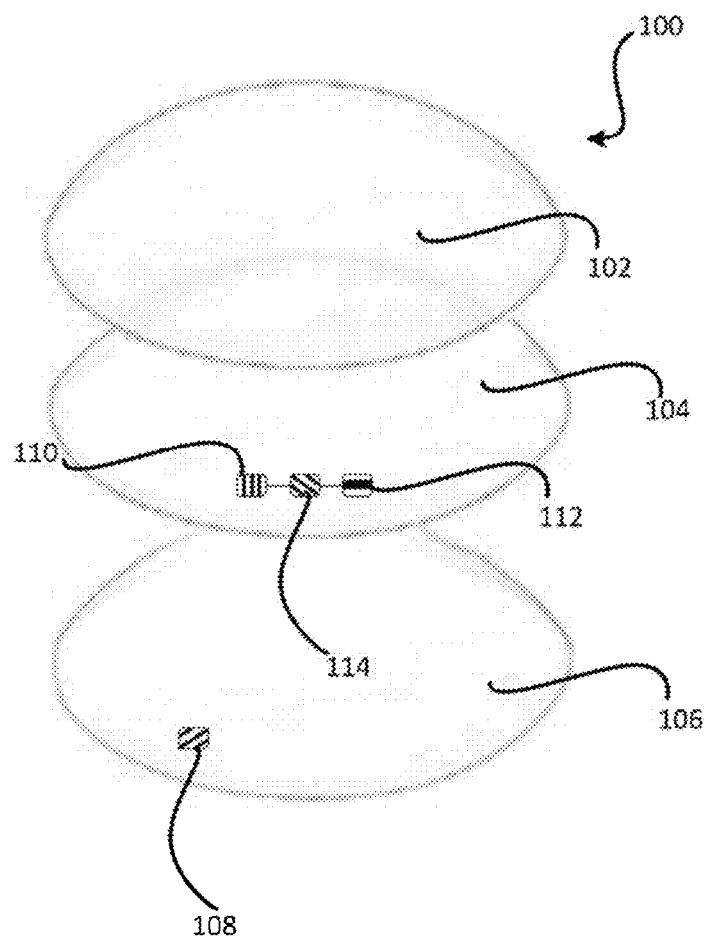
FIG. 10 is an expanded view of the contact lens.

An alternative approach to find the effect of varying angle was proposed where an electric field was plotted to show the efficiency of the reflection band light. A region of air was added to the geometry in order that the reflected band gap light could be observed. The geometry was tested with a range of angles (see FIGS. 9A-9C). Light was incident from the far left boundary and all exterior edges were set as scattering boundary conditions. The photonic crystal was of the same configuration as in the previous simulation. At a 15° slant, the photonic crystal resonated at 550 nm. This was evidenced by that fact that the reflected, angled light was most defined at this wavelength, and was also in agreement with the position of the band gap in FIG. 8C. The intensity decreased at 450 nm and 650 nm where barely any reflected light was seen. As the wavelength shifts from the resonant frequency, the intensity of the reflected light diminished.

The invention claimed is:

1. A contact lens, comprising:
   a photonic crystal comprising:
   a plurality of metal nanoparticle stacks comprising metal nanoparticles, wherein the plurality of metal nanoparticle stacks are spaced such that each metal nanoparticle stack of the plurality of metal nanoparticle stacks is substantially parallel to one another, and wherein a distance between adjacent metal nanoparticle stacks increases or decreases in response to a concentration of an analyte thereby producing a shift in a photonic band gap and a color change in the photonic crystal;
   a sensor for measuring the shift in the photonic band gap, and
   a hydrogel matrix comprising polyhydroxyethylmethacrylate;
   wherein the plurality of metal nanoparticle stacks is arranged within the hydrogel matrix.

2. The contact lens of claim 1, wherein the metal nanoparticles comprise at least one metal selected from a group consisting of silver, gold, titanium, platinum, iron, cobalt, chromium, molybdenum, vanadium, tin, nickel, and niobium.

3. The contact lens of claim 1, wherein each metal nanoparticle stack of the plurality of metal nanoparticle stacks comprises 20-200 metal nanoparticles.

4. The contact lens of claim 1, wherein the photonic crystal comprises up to 100 metal nanoparticle stacks.

5. The contact lens of claim 4, wherein the photonic crystal comprises 3-6 metal nanoparticle stacks.

6. The contact lens of claim 1, wherein the distance between adjacent metal nanoparticle stacks is in a range of 140-250 nm.

7. The contact lens of claim 1, wherein the plurality of metal nanoparticle stacks has a tilt angle in a range of 1-30° measured from a plane of a metal nanoparticle stack to a surface plane of the photonic crystal.

8. The contact lens of claim 1, wherein the metal nanoparticles are spherical.

9. The contact lens of claim 1, wherein the metal nanoparticles have an average diameter in a range of 2-20 nm.

10. The contact lens of claim 9, wherein the average diameter of the metal nanoparticles varies between each metal nanoparticle stack.

11. The contact lens of claim 1, wherein the metal nanoparticles are randomly dispersed within each metal nanoparticle stack.

12. The contact lens of claim 1, wherein each metal nanoparticle stack of the plurality of metal nanoparticle stacks comprises metal nanoparticles of monodisperse diameter.

13. The contact lens of claim 1, wherein the shift in the photonic band gap is reversible.

14. The contact lens of claim 1, wherein the color change is reversible.

15. The contact lens of claim 1, wherein the analyte is glucose.

16. A method for detecting a glucose concentration of a subject, the method comprising:
   wearing the contact lens of claim 1, thereby contacting the contact lens to tears produced by the subject; and
   detecting the shift in the photonic band gap.

17. The method of claim 16, wherein the photonic crystal changes color in response to the glucose concentration in the tears.

18. The method of claim 16, wherein the subject has diabetes.

19. The contact lens of claim 1, wherein the metal nanoparticle stacks are spaced such that each metal nanoparticle stack of the plurality of metal nanoparticle stacks is aligned to one another at no more than 5° from parallel.

20. The contact lens of claim 1, wherein the metal nanoparticle stacks are spaced such that each metal nanoparticle stack of the plurality of metal nanoparticle stacks is aligned parallel to one another.

* * * * *